US006450049B1

(12) United States Patent
Menguc

(10) Patent No.: US 6,450,049 B1
(45) **Date of Patent: *Sep. 17, 2002**

(54) GLASS RUN SEAL TESTING MACHINE

(75) Inventor: Ismail Menguc, Brighton, MI (US)

(73) Assignee: SaarGummi Americas, Inc., Ann Arbor, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/821,866

(22) Filed: Mar. 30, 2001

Related U.S. Application Data

(63) Continuation of application No. 09/392,919, filed on Sep. 9, 1999.

(51) Int. Cl.[7] .................................................. G01N 19/00

(52) U.S. Cl. ................................ 73/866.9; 73/7; 73/866

(58) Field of Search ................................ 73/7, 9, 865.3, 73/865.5, 865.9, 866

(56) References Cited

U.S. PATENT DOCUMENTS 4,672,844 A * 6/1987 Meyer ........................ 73/118.1
5,936,167 A * 8/1999 Kulig et al. ............... 73/865.6
5,950,144 A * 9/1999 Hall et al. .................. 702/108
6,269,705 B1 * 8/2001 Menguc ...................... 73/865.9

FOREIGN PATENT DOCUMENTS

DE 2651959 * 5/1978 ............ G01M/7/00
GB 2 247 956 * 3/1992 ............ G01N/3/08

* cited by examiner

*Primary Examiner*—Hezron Williams
*Assistant Examiner*—Charles D Garber
(74) *Attorney, Agent, or Firm*—Young & Basile, P.C.

(57) ABSTRACT

A window seal testing machine for seals of the type used in powered automotive windows, the testing machine comprising an adjustable frame simulating a portion of a powered automotive window, the frame being adapted to receive one or more sets of window seals and a piece of window glass therein to simulate the sealing relationship between the seals and window glass in an actual automotive window. The testing machine further includes a drive mechanism for repetitively cycling the window glass through the frame and seals to simulate actual window operation over hundreds or thousands of cycles. The entire machine is preferably self-contained and portable, and the frame is further adjustable to be adapted to test different sets of seals and types of window glass.

18 Claims, 5 Drawing Sheets

FIG-5
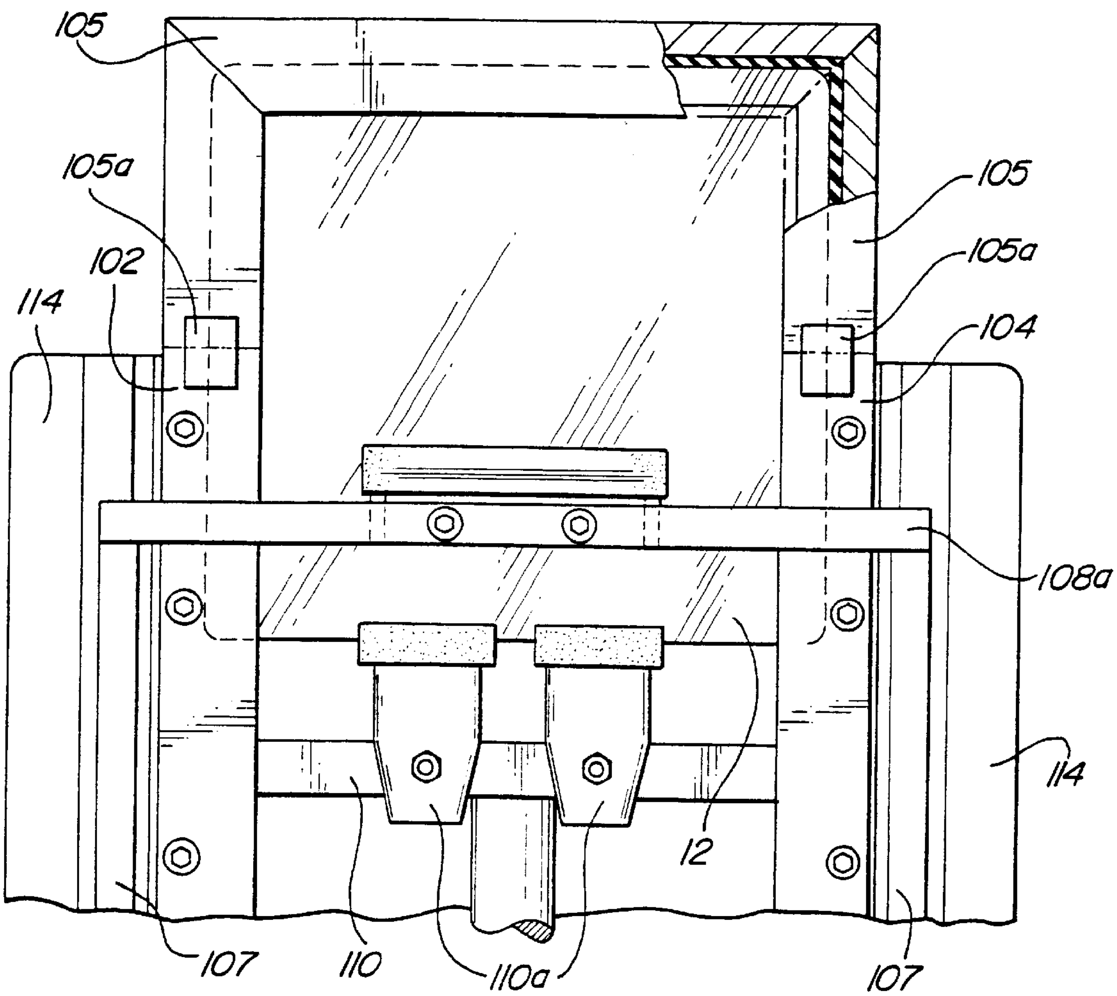
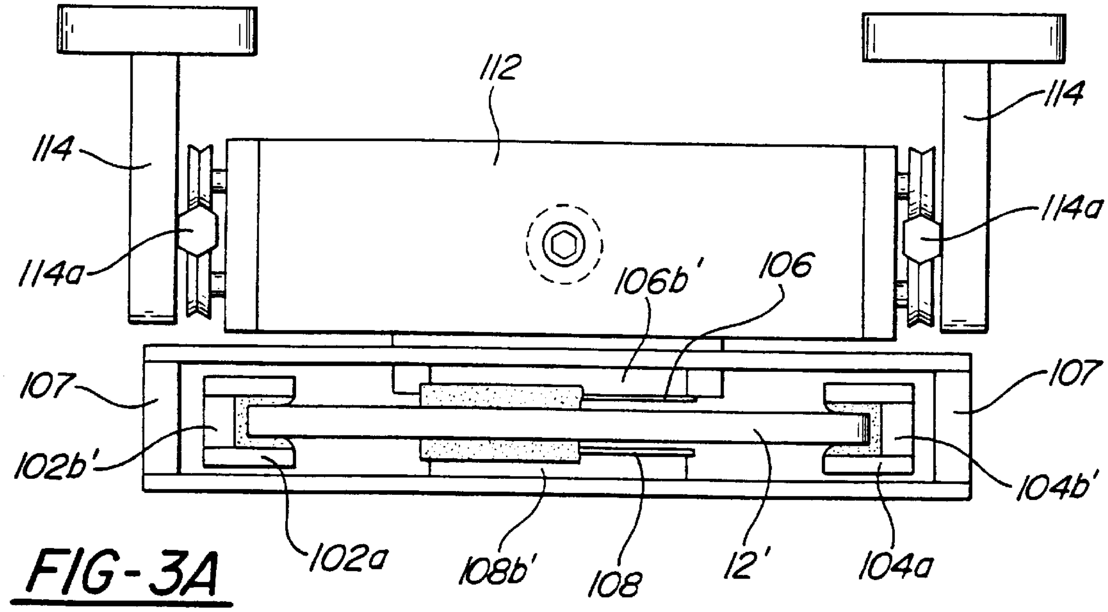
FIG-3A

GLASS RUN SEAL TESTING MACHINE

RELATED APPLICATIONS

The present application is a continuation of U.S. Ser. No. 09/392,919 filed Sep. 9, 1999.

FIELD OF THE INVENTION

The present invention is in the field of testing movable window seals of the type found in sliding vehicle windows.

BACKGROUND OF THE INVENTION

The "glass run" in an automobile door is the rubber seal mounted in the sliding window channel in the window frame. There is usually a "belt seal" along the lowermost edge of the window frame through which the window is extended and retracted from the interior of the door.

The sliding/wiping seal fit between the glass run and belt seals and the edges of the window creates frictional wear on the seals, which are expected to withstand tens or hundreds of thousands of cycles while maintaining an effective seal with the window. The reliability of the seals and their resistance to wear is therefore critical to the long-term operation of the entire window assembly. In an automobile the window assembly is a fairly integral part of the door, and repair or replacement of the seals can be difficult and expensive.

The current method of testing the effectiveness and wear life of the glass run and belt seals is to put the seals in an actual production-line door and to test them over hundreds or thousands of cycles at the automobile manufacturer's facility. There are a number of problems with this method. First, if the seal is defective, the entire door and window frame must be disassembled, and the seal must be replaced, returned and diagnosed by the seal manufacturer. Second, this testing method cannot anticipate the minimum and maximum tolerance variations from door to door. Third, the window actuator motors are prone to failure, and because they overheat easily they are operated for seal testing at about one cycle per minute. This is very slow when a seal's failure limit of tens of thousands of cycles is being tested.

Another difficulty in testing glass run seals is the frequent need to test them under specific environmental conditions, for example hot conditions simulating desert use and cold conditions simulating winter use. Current methods of testing make it difficult and expensive to test under these conditions.

SUMMARY OF THE INVENTION

In its broadest form the invention is a machine for testing glass run seals with a simulated, adjustable-tolerance window frame, using an associated high cyclic rate drive to reciprocate the window glass in the simulated frame's glass run. The simulated glass run holds sample seals, and is preferably adjustable to accommodate different seals or to vary seal tolerances.

In a preferred form the inventive testing machine is a self-contained unit comprising both the simulated glass run and window drive. The self-contained machine can be mounted on wheels for portability, for example allowing the testing machine to be rolled into an environmental test chamber simulating a real life window operating environment.

In a further preferred form the window drive is not an actual door-mounted window actuator, but a stronger, faster, adjustable speed motor, much more robust than the typical window actuator. Rather than operating at one cycle per minute as is done with the easily-overheated window actuators, the testing machine drive motor has been used to cycle the window as fast as twelve cycles per minute, greatly reducing test time.

In another preferred embodiment, the simulated glass run comprises an easily-adjusted set of spacers and seal mounts simulating the vertical glass run channels on the sides of the window, and optionally the upper edge of the window and the belt seal along the lower edge. By adjusting spacers in the frame, or by adjusting the frame itself, the simulated glass run can be adapted to test both different seals and different window types or models.

In a further preferred form a wear-measuring device such as a load cell is mounted in the drive system to measure progressive changes in window closing effort between the window and seals over hundreds or thousands of cycles.

These and other features and advantages of the present invention will become apparent upon further reading of the specification and in view of the accompanying drawings of a preferred, illustrative embodiment.

SUMMARY OF THE INVENTION

FIG. 5 is a front elevational view of the glass run simulating portion of the machine shown in FIG. 2, with an optional seal mount simulating the top edge or "upper line" of a window frame;

FIG. 3A is a plan view of the glass run simulating portion of FIG. 2, with the glass run simulating spacers and seal mounts adjusted for a thicker window and wider seals;

DETAILED DESCRIPTION OF THE ILLUSTRATED EMBODIMENTS

Figure 1:
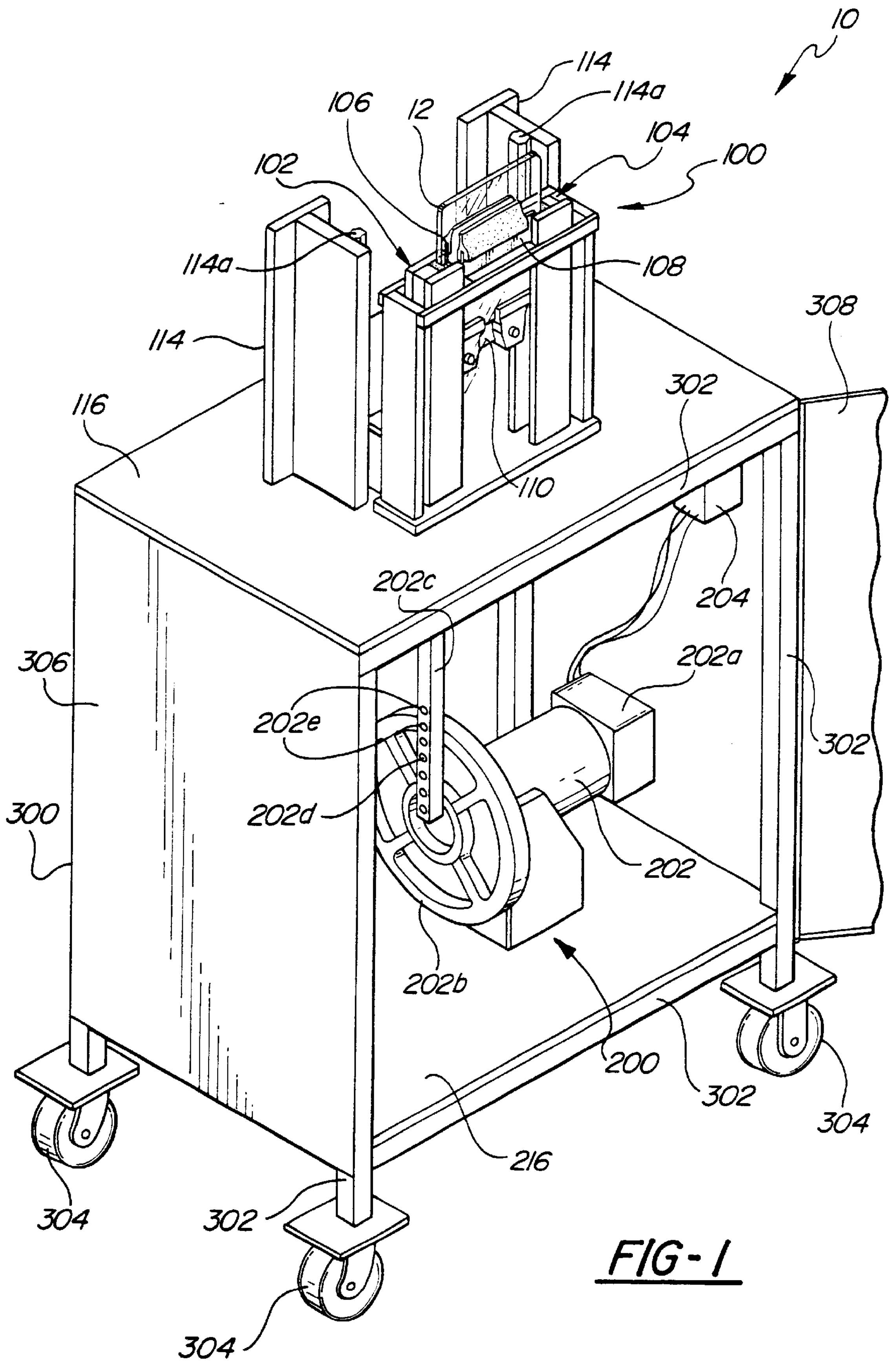
FIG. 1 is a perspective front view of a glass run seal testing machine according to a preferred, self-contained, portable embodiment of the invention.

Referring first to FIG. 1, a preferred example of a glass run seal testing machine according to the present invention is denoted generally by reference numeral 10. Illustrated testing machine 10 is in the form of a self-contained, portable cart-type unit which can be conveniently moved around a testing facility or in and out of an environmental testing chamber. It generally comprises an adjustable glass run simulating frame 100 on its upper end, and a drive system 200 for reciprocating window glass 12 up and down in frame 100, with both frame 100 and drive system 200 being integrated as a self-contained unit in housing 300.

It will be understood by those skilled in the art that although the preferred embodiment of the invention is self-contained and portable as illustrated, it is equally useful in a fixed setting. It may also be possible to provide frame 100 and drive system 200 separately, coupling them for testing only as necessary, depending on the nature of the test location and the type of drive system employed.

Figure 2:
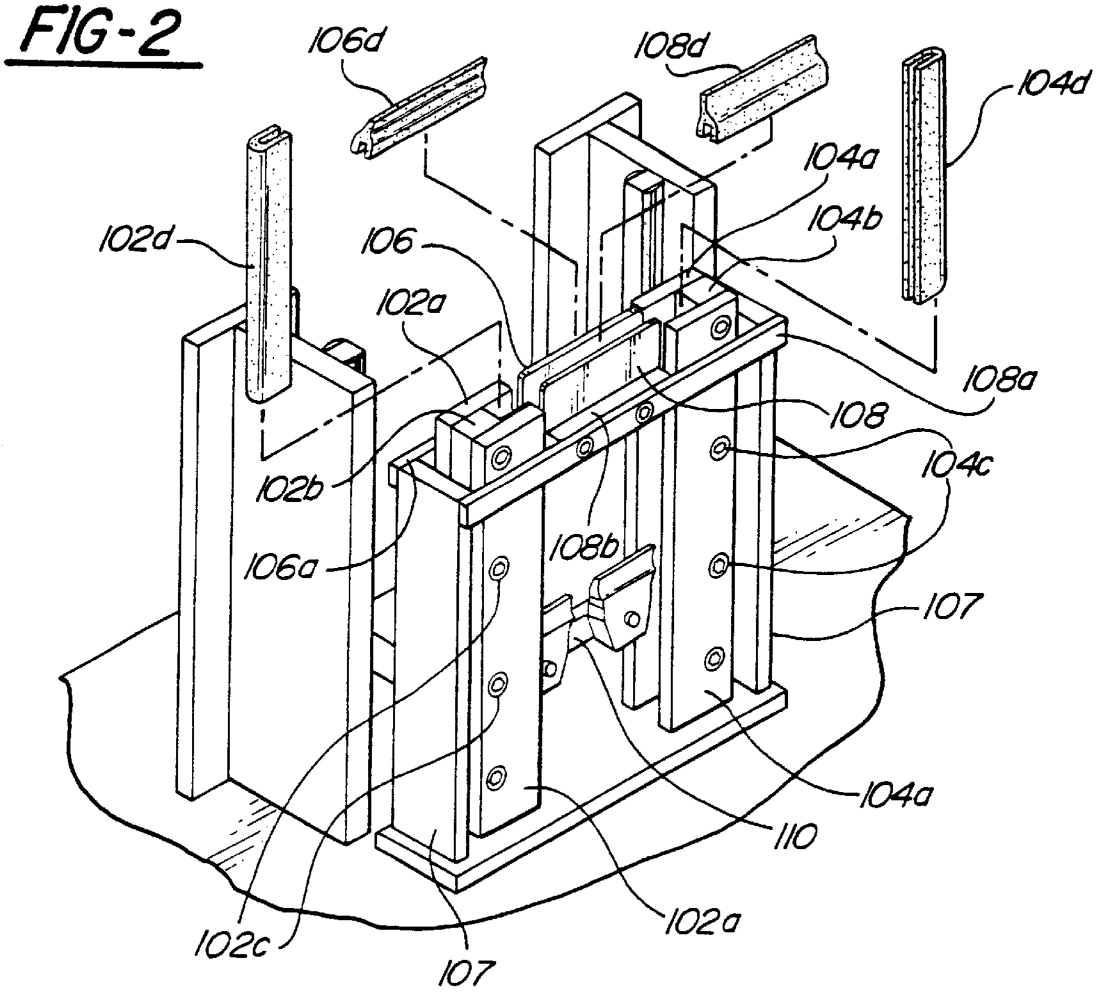
FIG. 2 is an enlarged view from the same perspective of the upper, glass run simulating portion of the machine of FIG. 1, with the seals being tested shown removed from their adjustable mounts.
Figure 3:
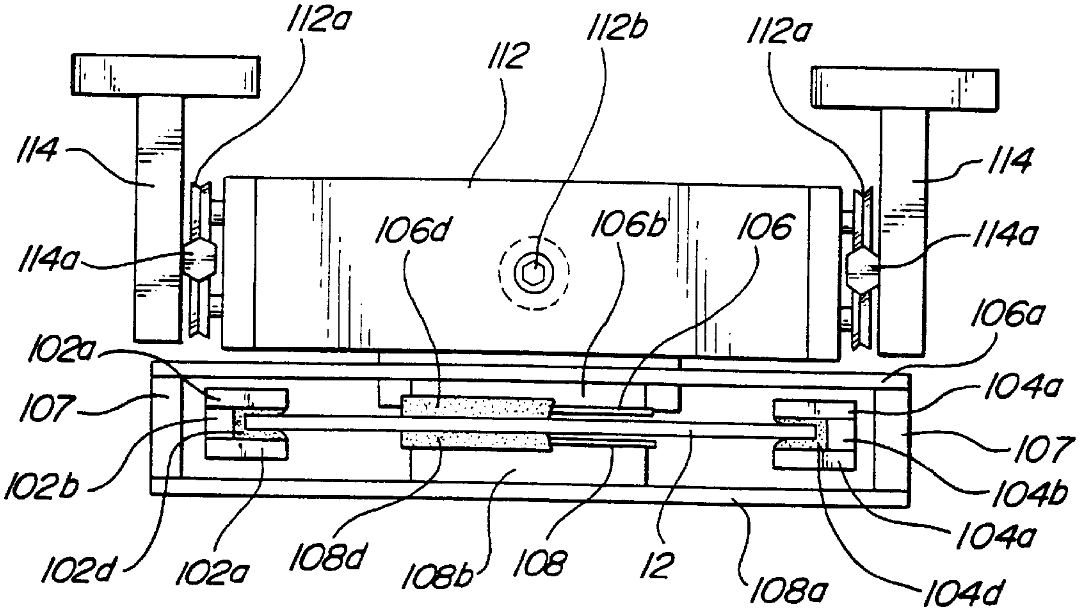
FIG. 3 is a plan view of the portion of the machine illustrated in FIG. 2.

Referring now to FIGS. 1, 2 and 3, glass run simulating frame 100 preferably comprises an adjustable frame whose dimensions can be varied to accommodate different types and thicknesses of window glass and glass run seals, so that it can be adapted for testing glass run seals intended for multiple makes and models of automobile. In the illustrated embodiment, frame 100 is generally made from rugged pieces of easily machined metal, such as aluminum, although other metals and even non-metals could be used in combination with or instead of the preferred aluminum material.

Frame 100 generally simulates the glass run channel in an automobile door, with an "A pillar" 102, a "B pillar" 104, an "inner belt strip" 106, and an "outer belt strip" 108. The simulated pillars 102 and 104 are designed to hold the glass run seals engaging the front and rear edges of the window, while the simulated inner and outer belt strips 106, 108 are designed to hold the belt seals engaging the inner and outer surfaces of the window glass.

Window glass 12 is positioned relative to frame 100 by a glass holder 110, illustrated as a pair of clamp-type mounts engaging the lower edge of window glass 12. Glass holder 110 is connected to a carriage 112 (FIG. 3) mounted for up and down motion on rail supports 114, in the illustrated embodiment with rollers 112*a* engaging rails 114*a* as best shown in FIG. 3. Carriage 112 in turn is connected to drive system 200 by a bolt or other suitable connection at 112*b*.

In the illustrated embodiment of FIG. 1, drive system 200 comprises a commercially available adjustable speed motor drive 202 with built-in gearbox 202*a*, a flywheel type adjustment wheel 202*b*, and a variable stroke drive arm 202*c* connected to the wheel by a suitable pin 202*d* mounted through one of several bushings 202*e*. Adjustable stroke drive arm 202*c* is preferably connected through a known mechanism for translating the oscillating crank-shaft type motion imparted by wheel 202*b* into vertical up/down motion, using a pivot-type coupling of known type (see FIGS. 6 and 7).

Motor drive 202 is powered through a regulated power supply 204, either AC or DC depending on the motor, and either self-contained (as in a battery-powered unit) or connected to an external power source (as in a voltage regulator or current adapter).

While the motor drive illustrated in FIG. 1 is a preferred type, it will be apparent to those skilled in the art that virtually any drive system capable of reciprocating window glass 12 up and down in frame 100 can be used, and many are available and are readily adapted to such a purpose.

All of the above-identified components of testing machine 10 are illustrated as being integrated in a cart-type support housing 300. Illustrated housing 300 comprises a tube-type frame 302 carrying upper and lower support plates 116, 216 for supporting frame 100 and drive system 200. Housing 300 is preferably portable, for example by way of illustrated caster wheels 304. Housing 300 may optionally be soundproofed and access-secured with side panels 306 and optional door 308.

The details of glass run simulating frame 100 are shown in FIGS. 2 and 3. Simulated side pillars 102 and 104 each comprise run channel side plates 102*a*, 104*a*; run channel spacer bars 102*b*, 104*b*; and in the illustrated embodiment are assembled with hex bolts 102*c*, 104*c* extending through the side plates and spacer bars for adjustment purposes described below.

The simulated inner and outer belt strips 106 and 108 in the illustrated embodiment are generally parallel metal plates mounted in the frame by belt seal uprights 106*a*, 108*a*; belt seal spacers 106*b*, 108*b*; and hex bolts 106*c*, 108*c*, which provide adjustability described below.

Still referring to FIGS. 2 and 3, glass run seals 102*d*, 104*d* are mounted frictionally and/or adhesively in simulated pillars 102 and 104, engaging the side edges of window glass 12 in known fashion for a sliding seal fit. Optionally, if the intended window assembly uses a belt seal, belt seal segments 106*d*, 108*d* are frictionally and/or adhesively secured on the top edges of belt-seal simulating plates 106 and 108 in known fashion, with their wiping seal edges engaged against the front and rear faces of window glass 12.

It will be understood by those skilled in the art that the testing machine of the present invention can be used to successfully test seals using only segments of actual glass run and belt seals, and using only a test-sized piece of window glass of the same thickness and material as the full-size window for which the seals are ultimately intended. Hence when the terms "seal" and "window" are used herein, they can be considered to include both full-size and test-size components or portions.

It will be understood by those skilled in the art that while a test-sized arrangement is preferred, it would also be possible to build frame 100 of sufficient size to handle full-size window glass and full-length glass run and belt seals, provided that the corresponding frame portions were sized and shaped accordingly. The generally rectangular, scaled-down version illustrated is preferred, however, for its adjustability, portability and ease of manufacture.

Figure 4:
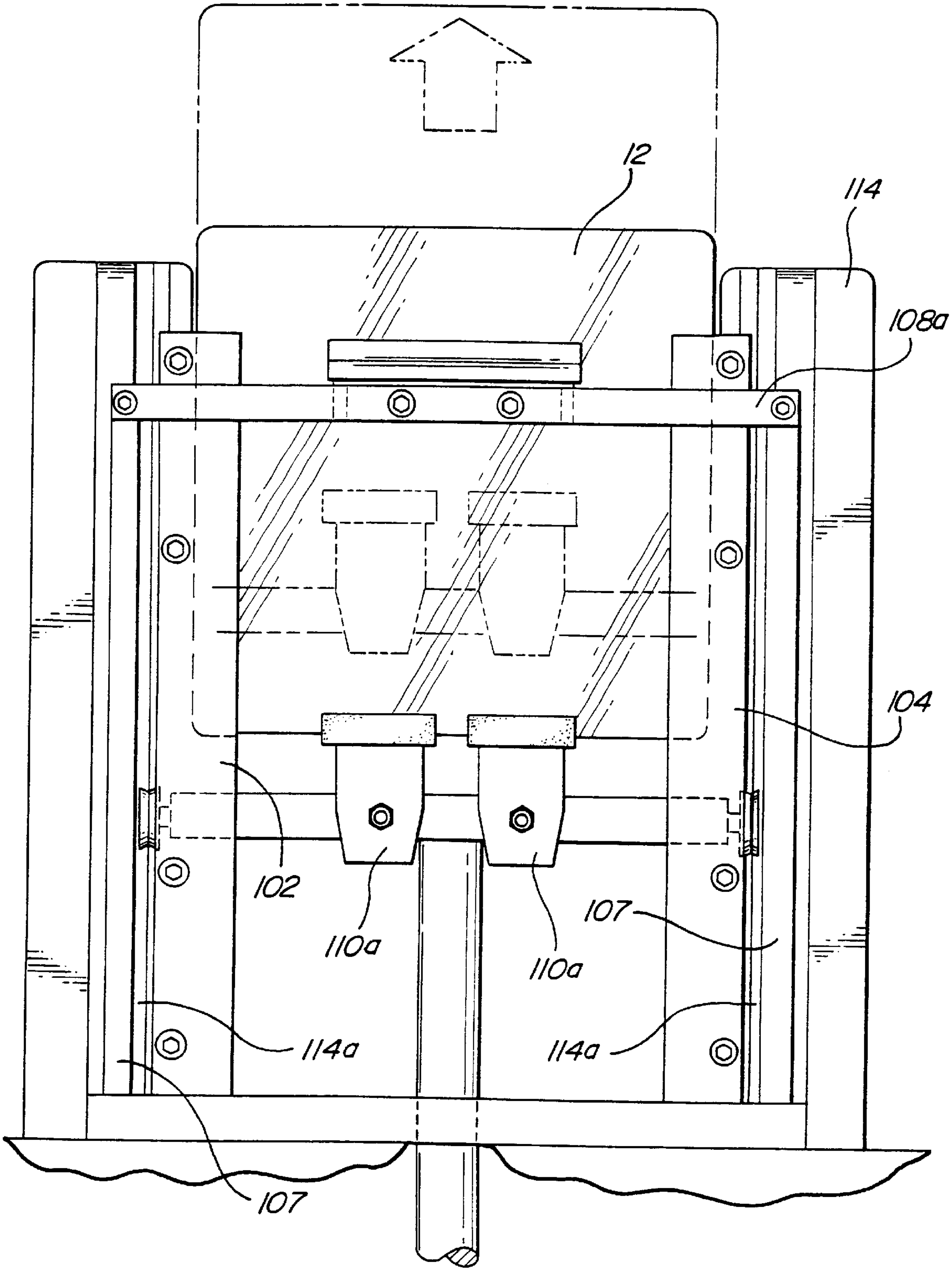
FIG. 4 is a front elevational view of the glass run simulating portion of the machine shown in FIG. 2, with the test window glass shown in both lowered and raised positions.

Referring next to FIG. 4, the up/down test motion imparted to window glass 12 by machine 10 is illustrated, with the down position of the window glass in solid lines and the up position in broken lines. It will be understood that this vertical up/down motion can be adjusted to accurately simulate window operation, seal resistance, and wear.

The tolerances and tension of the seals relative to the simulated frame and window glass can be adjusted with the hex bolts holding the various portions of the frame together, or by replacing the various spacer bars 102*b*, 104*b*, 106*b*, 108*b* corresponding to the glass run and belt seals. This is best illustrated by a comparison of FIGS. 3 and 3A, in which FIG. 3 represents a test of a first piece of window glass 12 with seals and spacers of commensurate thickness and spacing, and FIG. 3A represents a test of a second, thicker piece of window glass 12' with differently-sized seals and spacers. The adjustability of frame assembly 100 allows the testing machine of the present invention to be reconfigured and adapted to test different combinations of window glass and seals in a matter of minutes using only simple hand tools.

The minimum and maximum tolerances intended for a particular set of seals and window glass can be tested by loosening or tightening the spacer hex bolts along some or all of the frame, or by replacing one or more of the glass run and belt seal spacers.

The open-ended frame assembly 100 illustrated in FIGS. 1–3 is of a type intended to simulate and test the "lower line" or bottom portion of a window. Referring to FIG. 5, it is also possible to adapt the invention to test the upper half of the vehicle window using a an upper glass run simulating frame portion 105, basically identical in construction to simulated pillar portions 102, 104. Top frame portion 105 may comprise one or several pieces, and is preferably removably locked to the upper ends of pillars 102, 104 by plates, clamps, or other known mechanical fastening devices.

Figure 6:
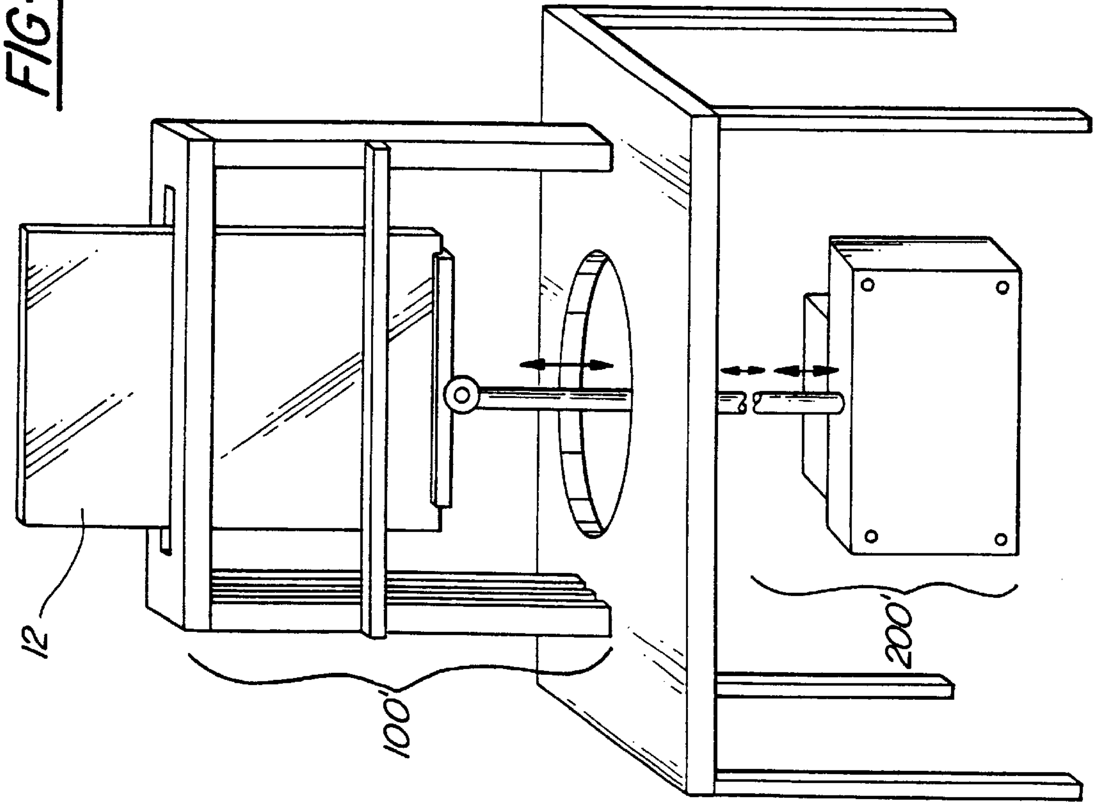
FIG. 6 is a schematic representation of the machine according to the invention; and, FIG. 7 is a schematic side elevational view of the lower, motor drive portion of the machine illustrated in FIG. 1, including an optional wear-measuring device connected to the drive system.

The foregoing is an illustrative example of a testing machine according to the invention. Referring to FIG. 6, a schematic representation of the invention is illustrated in simplified form. The invention is not limited to the particular embodiment illustrated in FIGS. 1–5, but resides more broadly in the concept of a glass run-simulating frame 100', preferably an adjustable frame, in which the seals can be mounted for relatively rapid, high cycle testing using an actual piece of window glass in a manner which allows seal life and other characteristics to be measured and diagnosed for actual seals and windows before they are assembled. In particular, the invention is not intended to be limited to any particular drive system 200' or carriage mechanism for the window glass in the frame, or to a drive system integrated with the frame in a housing.

Figure 7:
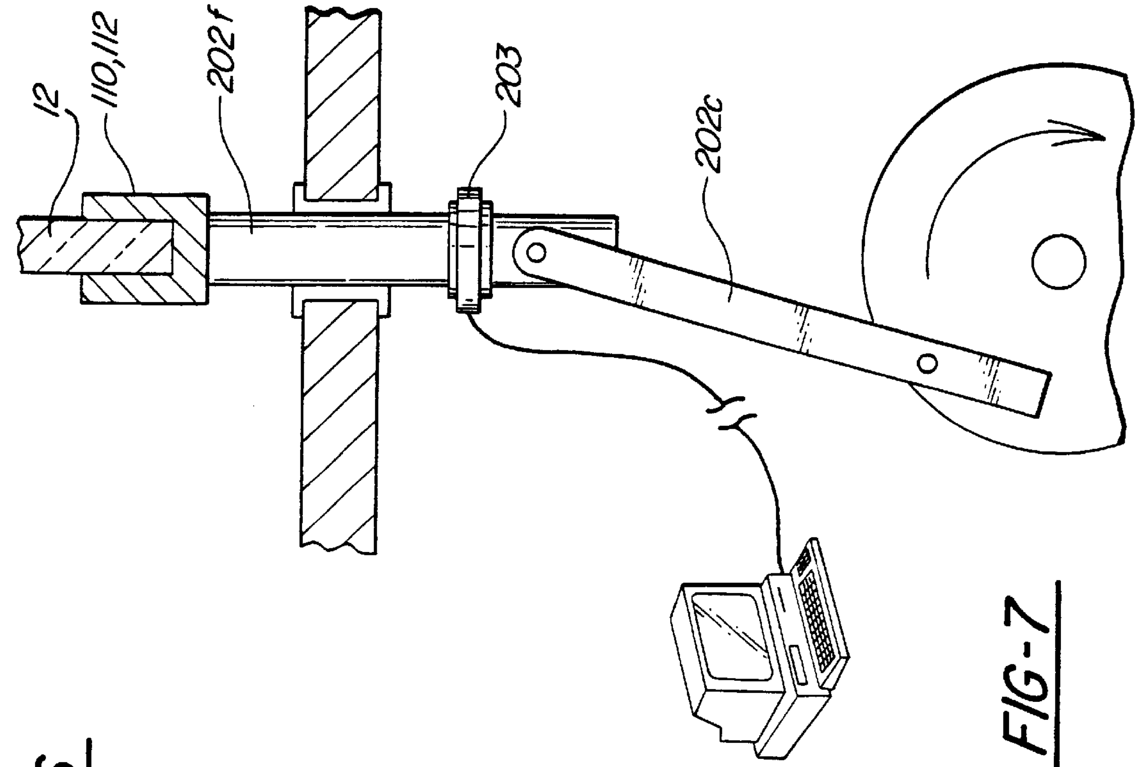

Referring next to FIG. 7, the illustrative drive linkage between drive system 200 and window glass 12 from FIG. 1 is shown to include an optional wear-measuring apparatus, in the illustrated embodiment in the form of a load cell 203 of commercially available type which is connected in-line with the stroke adjustment arm 202*c* and vertical drive coupling 202*f* to measure the frictional force exerted by the glass run and belt seals on window glass 12 over a life of thousands of cycles. Load cell 203 sends analog voltage signals via path 203*a* to a monitor or calculating device such as a computer to gauge, store and/or compare the signals for life-cycle evaluating purposes. Sudden increases in force measured by the load cell may indicate seal and/or window friction-coating wear.

Since the foregoing represent certain preferred embodiments of the invention, and since various modifications and changes can be made to the illustrated embodiment without departing from the invention, the scope of the invention is not to be limited except by the scope of the following claims.

Accordingly, I claim:

1. An apparatus for testing glass window seals of the type used in powered automotive windows, comprising:

a frame adapted to receive a piece of test sized piece of window glass driven in a repetitive motion simulating operation in a powered automotive window, the frame comprising a pair of seal-holding members adapted to removably mount a pair of window seal segments in a position engaging the window glass in a manner simulating a sliding seal with the window glass in a powered automotive window, the window seal segments being taken from the group consisting of glass run seals and belt seals, the seal holding members having opposing members for capturing said window seal segments wherein the distance between said opposing members is adjustable to removably mount different pairs of window seal segments and to vary tolerances with which the window seals engage the window glass.

2. The apparatus of claim 1, wherein the seal-holding members comprise a pair of pillar-simulating members each adapted to hold a glass run seal.

3. The apparatus of claim 2, wherein the seal-holding members further comprise a pair of belt seal simulating members located adjacent inner and outer surfaces of the window glass, respectively, and between the pillar-simulating members.

4. The apparatus of claim 1, wherein the seal-holding members comprise a pair of belt-seal simulating members located adjacent inner and outer surfaces of the window glass, respectively.

5. The apparatus of claim 4, wherein the belt seal simulating members are adjustably attached to the frame to vary the spacing between them and the inner and outer surfaces of the window glass.

6. The apparatus of claim 5, wherein the belt seal simulating members are adjustably attached to the frame by removable spacer bars.

7. The apparatus of claim 1, wherein the frame is open-ended such that upper ends of the seal-holding members, the window seal segments, and the window glass are exposed for observation and access.

8. The apparatus of claim 7, wherein the open-ended frame is configured to simulate a lower line portion of a powered automotive window, and further including a top frame portion simulating an upper line portion of a powered automotive window and capable of being mated with the open-ended frame simulating the lower-line portion, the mated top and open-ended frame portions together simulating a complete powered automotive window, the top frame portion being adapted to removably mount one or more upper line window seal segments.

9. The apparatus of claim 1, wherein the window driving member is connected to a window drive mounted together with the frame on a common support housing.

10. The apparatus of claim 1, wherein the window is driven by a variable speed motor capable of driving the window glass in the repetitive motion at a cyclic rate greater than a cyclic rate possible with a window actuator in a powered automotive window.

11. The apparatus of claim 10, wherein the motor includes a seal wear-measuring sensor.

12. The apparatus of claim 11, wherein the seal wear-measuring sensor comprises a load cell connected to a drive member in line with the motor and window glass.

13. An apparatus for testing glass window seals of the type used in powered automotive windows, comprising;

a frame adapted to receive a test sized piece of window glass driven in a repetitive motion simulating operation in a powered automotive window, the frame comprising a pair of seal-holding members adapted to removably mount a pair of window seal segments in a position engaging the window glass in a manner simulating a sliding seal with the window glass in a powered automotive window, the window seal segments being taken from the group consisting of glass run seals and belt seals, the seal holding members being adjustable to removeably mount different pairs of window seal segments and to vary tolerances with which the window seal segments engage the window glass, wherein the seal holding members comprise a pair of pillar-simulating members each adapted to hold a glass run seal wherein the pillar-simulating members each comprise a pair of glass run channel sides adjustably spaced relative to one another and located to overlie side edges of the window glass.

14. The apparatus of claim 13, wherein the glass run channel sides are spaced by a removable spacer bar.

15. A method for testing glass window seals of the type used in powered automotive windows, comprising the following steps:

mounting one or more segments of actual window seals in an adjustable open-ended frame simulating powered automotive window channel portions from the group consisting of glass run channels and belt strips;

mounting a test-sized piece of window glass in the frame in engagement with the window seal segments in a manner simulating an actual sliding seal in a powered automotive window;

driving the window glass in the frame in a repetitive motion simulating actual powered automotive window operation cycles; and, observing wear on the window seal segments over a period of many cycles.

16. The method of claim 15, further including the step of adjusting tolerances of the window seal segments in the frame between minimum and maximum tolerances intended for the window seal segments in an actual powered automotive window.

17. The method of claim 15, wherein the adjustable open-ended frame is part of a self-contained testing machine including a powered mechanism for driving the window glass in the frame, the testing machine further being portable, wherein the testing machine is placed in an environmental chamber for simulating actual powered automotive window operation under a particular environmental condition.

18. The method of claim 15, wherein the open-ended frame includes adjustable seal-holding members capable of being adjusted to mount window seals for different windows, and further including the step of replacing a first set of window seals and a first piece of window glass and installing a second set of window seals and a second piece of window glass in the frame, and testing the second set of window seals with the second piece of window glass in the frame.

* * * * *

UNITED STATES PATENT AND TRADEMARK OFFICE

CERTIFICATE OF CORRECTION

PATENT NO. : 6,450,049 B1
DATED : September 17, 2002
INVENTOR(S) : Menguc

It is certified that error appears in the above-identified patent and that said Letters Patent is hereby corrected as shown below:

Column 4,
Line 67, delete the word "a" before the word "an"

Column 5,
Line 61, delete claim 3 and insert:
3. An apparatus for testing glass window seals of the type uesd in powered automotive windows, comprising;

a frame adapted to receive a test sized piece of window glass driven in a repetitive motion simulating operation in a powered automotive window, the frame comprising a pair of seal-holding members adapted to removably mount a pair of window seal segments in a position engaging the window glass in a manner simulating a sliding seal with the window glass in a powered automotive window, the window seal segments being taken from the group consisting of glass run seals and belt seals, the seal holding members being adjustable to removeably mount different pairs of window seal segments and to vary tolerances with which the window seal segments engage the window glass, wherein the seal holding members comprise_a pair of pillar-simulating members each adapted to hold a glass run seal wherein the pillar-simulating members each comprise a pair of glass run channel sides adjustably spaced relative to one another and located to overlie side edges of the window glass.

Line 66, delete claim 4 and insert:
4. The apparatus of claim 3, wherein the glass run channel sides are spaced by a removable spacer bar.

UNITED STATES PATENT AND TRADEMARK OFFICE

CERTIFICATE OF CORRECTION

PATENT NO. : 6,450,049 B1
DATED : September 17, 2002
INVENTOR(S) : Menguc

It is certified that error appears in the above-identified patent and that said Letters Patent is hereby corrected as shown below:

<u>Column 6,</u>
Line 36, delete claim 13 and insert:
13. The apparatus of claim 12, wherein the motor includes a seal wear-measuring sensor.

Signed and Sealed this

Fourteenth Day of January, 2003

JAMES E. ROGAN
*Director of the United States Patent and Trademark Office*